US011275936B2

(12) United States Patent
Neumann

(10) Patent No.: US 11,275,936 B2
(45) Date of Patent: Mar. 15, 2022

(54) SYSTEMS AND METHODS FOR CLASSIFICATION OF SCHOLASTIC WORKS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 75 days.

(21) Appl. No.: 16/912,126

(22) Filed: Jun. 25, 2020

(65) Prior Publication Data

US 2021/0406535 A1 Dec. 30, 2021

(51) Int. Cl.
*G06K 9/00* (2006.01)
*G06K 9/62* (2022.01)

(52) U.S. Cl.
CPC ..... *G06K 9/00483* (2013.01); *G06K 9/00463* (2013.01); *G06K 9/00469* (2013.01); *G06K 9/6256* (2013.01)

(58) Field of Classification Search
CPC ........... G06K 9/00483; G06K 9/00463; G06K 9/00469; G06K 9/6256
USPC ................................ 382/159, 176, 224–225
See application file for complete search history.

(56) References Cited

U.S. PATENT DOCUMENTS

| | | | |
|---|---|---|---|
| 6,802,810 B2 | 10/2004 | Ciarniello et al. | |
| 8,594,948 B2 | 11/2013 | McGlennen et al. | |
| 8,655,817 B2 | 2/2014 | Hasey et al. | |
| 8,812,244 B2 | 8/2014 | Angelides | |
| 9,092,391 B2 | 7/2015 | Stephan et al. | |
| 10,152,702 B2 | 12/2018 | Ingber | |
| 10,839,013 B1 * | 11/2020 | Werris | G06F 16/383 |
| 2005/0075543 A1 | 4/2005 | Calabrese | |
| 2008/0059224 A1 | 3/2008 | Schechter | |
| 2014/0162887 A1 | 6/2014 | Martin et al. | |
| 2015/0019241 A1 | 1/2015 | Bennett et al. | |
| 2015/0177250 A1 | 6/2015 | Leontovich et al. | |
| 2017/0236281 A1 | 8/2017 | Dacosta | |

(Continued)

OTHER PUBLICATIONS

Chui, et al., Disease Diagnosis in Smart Healthcare: Innovation, Technologies and Applications, journal, Dec. 18, 2017, vol. 9, issue 12.

*Primary Examiner* — Daniel G Mariam
(74) *Attorney, Agent, or Firm* — Caldwell Intellectual Property Law; Keegan Caldwell; Katherine Rubino

(57) ABSTRACT

A system for classification of scholastic works includes a computing device configured to receive a first scholastic work, identify an author and a category of the first scholastic work, determine at least a work theme by receiving theme training data, the theme training data including a plurality of entries, each entry including a training textual element and a correlated theme, training a theme classifier as a function of the training data, and determining the at least a work theme as a function of the plurality of textual elements and the theme classifier, calculate a reliability quantifier as a function of the at least a theme, the author, and the category, select the scholastic work as a function of the reliability quantifier, derive, from the scholastic work, at least a correlation between a diagnostic element and a practice, and store the at least a correlation in an expert database.

20 Claims, 6 Drawing Sheets

(56) References Cited

U.S. PATENT DOCUMENTS

2018/0365383 A1 12/2018 Bates
2019/0088366 A1 3/2019 Vaughan et al.

* cited by examiner

SYSTEMS AND METHODS FOR CLASSIFICATION OF SCHOLASTIC WORKS

FIELD OF THE INVENTION

The present invention generally relates to the field of language processing. In particular, the present invention is directed to systems and methods for classification of scholastic works.

BACKGROUND

A wealth of data exists in the form of scientific and/or medical research that has the potential as training data to generate classifiers or other models suitable for diagnostic or other procedures. Unfortunately, much of this data is not in a useful form for efficient analysis, placing it beyond the reach of existing solutions.

SUMMARY OF THE DISCLOSURE

In an aspect, a system for classification of scholastic works includes a computing device, wherein the computing device is configured to receive a first scholastic work including a plurality of textual elements, identify an author and a category of the first scholastic work, determine at least a work theme, wherein determining further includes receiving theme training data, the theme training data including a plurality of entries, each entry including a training textual element and a correlated theme, training a theme classifier as a function of the training data, and determining the at least a work theme as a function of the plurality of textual elements and the theme classifier, calculate a reliability quantifier as a function of the at least a theme, the author, and the category, select the scholastic work as a function of the reliability quantifier, derive, from the scholastic work, at least a correlation between a diagnostic element and a practice, and store the at least a correlation in an expert database.

In another aspect, a method of classification of scholastic works includes receiving, at a computing device, a first scholastic work including a plurality of textual elements, identifying, by the computing device, an author and a category of the first scholastic work, determining, by the computing device, at least a work theme, wherein determining further comprises receiving theme training data, the theme training data including a plurality of entries, each entry including a training textual element and a correlated theme, training a theme classifier as a function of the training data, and determining the at least a work theme as a function of the plurality of textual elements and the theme classifier, calculating, by the computing device, a reliability quantifier as a function of the at least a theme, the author, and the category, selecting, by the computing device, the scholastic work as a function of the reliability quantifier, deriving, by the computing device and from the scholastic work, at least a correlation between a diagnostic element and a practice, and storing, by the computing device the at least a correlation in an expert database.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments disclosed herein analyze scholastic works to determine fields of applicability as well as reliability of such works. Correlations may be derived from scholastic works for use in training data and/or other applications in machine learning, and/or for storage in expert databases suitable for use in various applications. In some embodiments, systems and methods described herein may generate further training data for iterative learning, powering increasingly accurate processes for producing increasingly good quality of derived data. System may further use unfavorable scholarship and/or retractions to detect situations where a give scholastic work should not be used in further training, and may remove such a work from storage underlying training data; this may further increase the ability to train expert systems or other machine-learning and/or database driven platforms in a manner that accounts for the evolving nature of knowledge as encapsulated in such works.

Figure 1:
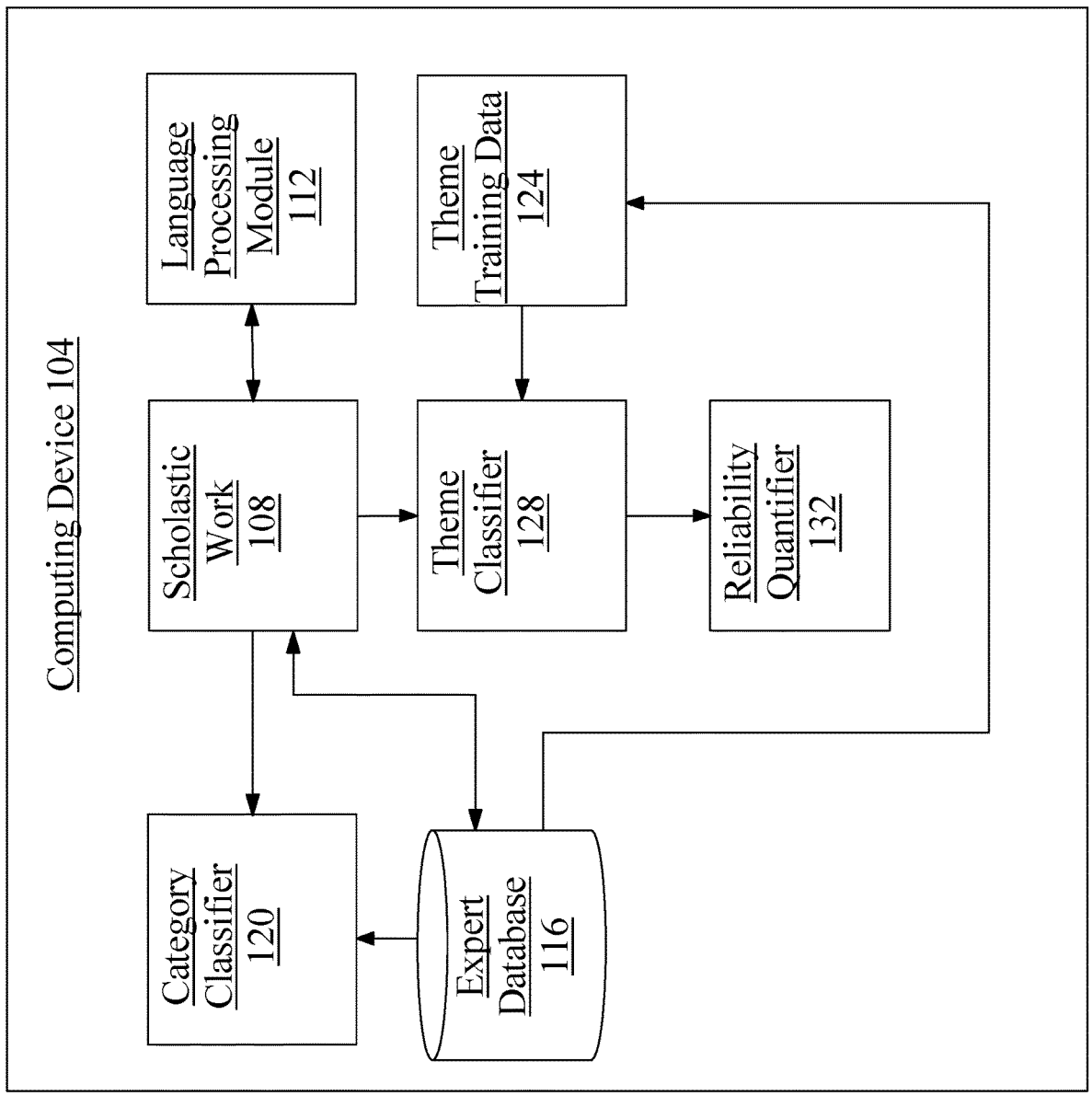
FIG. 1 is a block diagram illustrating an exemplary embodiment of a system for classification of scholastic works.

Referring now to FIG. 1, an exemplary embodiment of a system 100 for classification of scholastic works is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device 104.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to receive a first scholastic work 108 including a plurality of textual elements. A "scholastic work," as used in this disclosure, is a document, article, and/or other body of text containing results of scientific and/or medical analysis and/or study. A scholastic work may include, without limitation, a peer-reviewed scientific and/or medical journal article, a non-peer reviewed journal article, a transcript and/or other description of proceedings at an academic, scientific, and/or medical conference, an article in a popular science magazine, a case study as published in a medical and/or scientific journal, a website entry penned by a scientist, clinician, or other expert author, or the like.

Continuing to refer to FIG. 1, computing device 104 may receive first scholastic work 108 in any suitable manner. Receiving may include receiving an entry of a file containing first scholastic work 108 by a user, who may be an expert user; user may download file from a service such as JSTOR as provided by Ithaka Harbors, Inc. of New York and/or from an online version of a journal. Alternatively or additionally, user may provide scholastic work from a portable memory device and/or another device connected to computing device 104 directly and/or by means of any wired or wireless network connection. As a further non-limiting example, receiving may include receiving in an electronic communication such as a feed or subscription service, by crawling and/or scraping Internet sites, or the like. Scholastic work may be entered into computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, computing device 104 may automatically obtain the document using such an identifier, for instance by submitting a request to a database or compendium of documents such as JSTOR as provided by Ithaka Harbors, Inc. of New York.

Further referring to FIG. 1, computing device 104 may parse scholastic work for a plurality of phrases. Parsing and/or other processes for extraction of phrases and/or textual elements may be performed, without limitation, by a language processing module 112. Language processing module 112 may include any hardware and/or software module. Language processing module 112 may be configured to extract, from the one or more documents, one or more words, phrases, sentences, paragraphs, and/or other textual elements. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module may compare extracted textual elements to one or more associated textual elements and/or to associations therewith, in a corpus of documents. In an embodiment, such associations may be enumerated, to find total count of mentions in such documents. Alternatively or additionally, language processing module may operate to produce a language processing model. Language processing model may include a program automatically generated by computing device 104 and/or language processing module to produce associations between one or more words extracted from at least a document and detect associations, including without limitation mathematical associations, between such textual elements. Associations between language elements, where language elements include for purposes herein extracted words or other textual elements may include, without limitation, mathematical associations, including without limitation statistical correlations between any language element and any other language element and/or language elements. Statistical correlations and/or mathematical associations may include probabilistic formulas or relationships indicating, for instance, a likelihood that a given detected and/or extracted textual element indicates another textual element. As a further example, statistical correlations and/or mathematical associations may include probabilistic formulas or relationships indicating a positive and/or negative association between at least an extracted word and other textual elements.

Further referring to FIG. 1, language processing module and/or computing device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Further referring to FIG. 1, language processing module may include a module generated per publication and/or per subject area, where publications, and thus scholastic works within such publications may be classified to subject areas. For instance, and without limitation, when a publication is encountered for the first time, a non-subject-specific language model may be used extract words, phrases, and/or scholastic works from issues of the publication; publication may be classified to one or more themes as described below which may include and/or be used to inform classification to subject areas. An language processing module developed and/or trained from such subject areas may be used thereafter to parse and/or otherwise process and/or analyze language from publication as classified, which classification may be stored in memory of computing device 104, using a subject-area language model for a subject area to which publication has been classified. Computing device 104 and/or other devices in and/or communicating with system 100 may periodically update and/or training any language processing module using any language processing methods and/or protocols as described above.

Still referring to FIG. 1, computing device 104 and/or language processing module may be configured to identify sections of scholastic work. Sections of scholastic work may include, without limitation, an abstract, a conclusion, a discussion section, an analysis section, an appendix, a bibliography, and/or any other distinct section of any scholastic work as described above. Identifications of sections may be performed by identifications of headings containing words associated with such sections, such as "Abstract," "Discussion," "Appendix I," or the like. Alternatively or additionally language processing module may detect textual elements such as words, phrases, sentences, and/or paragraphs having a high degree of vector similarity and/or other close association with such sections; this may enable computing device 104 and/or language processing module to detect a section in circumstances in which the section does not contain a particular keyword ordinarily associated therewith, and/or in which it is not feasible to distinguish section headings from other text.

With continued reference to FIG. 1, computing device 104 is configured to identify at least an author of scholastic work. In an embodiment, each author of scholastic work may be identified in an "authors" section and/or by one or more words indicative of authorship such as "by" at a section of scholastic work such as a title page, footer, or the like. Authors may be separately identified by a database such as JSTOR. Authors may be identified in metadata. Authors may be entered manually by a user uploading and/or transmitting scholastic work to computing device 104. Persons skilled in the art, upon reviewing the entirety of this disclosure, will be aware of various alternative or additional ways in which authors may be identified by computing device 104, consistently with this disclosure.

Further referring to FIG. 1, computing device 104 may be configured to identify a category of scholastic work. A "category" of a scholastic work, as used in this disclosure, is a kind of article and/or document indicating its role in scientific and/or medical research, such as is suitable, for instance, to distinguish peer-reviewed work from expository and/or speculative work. A category may include, without limitation, a peer-reviewed journal article, a non-peer reviewed journal article, a journal article that has review pending, a non-journal scientific article, a popular science article, a news article, a webpage, or the like. Each category may be broken into further sub-categories such as without limitation a recommendation, a case study, a proposed treatment, diagnostic data, research results, or the like. In an embodiment, text in and/or associated with scholastic work may indicate a category thereof, for instance, in a peer-reviewed journal, a given work may be identified as a peer-reviewed by a heading indicating it is an "article," while another category such as proceedings of a conference, a review, an editorial commentary, or the like may be so denoted as well. As a further non-limiting example, where scholastic work is provided by a subscription service, database, and/or expert user, such subscription service, database, and/or expert user may indicate a category to which scholastic work does and/or does not belong, such as differentiating between peer-reviewed work and non-peer-reviewed work, distinguishing between various forms of the latter, or the like. Publications may further indicate and/or be associated with indications in databases, including an expert database as described in further detail below, identifying such publications as peer-reviewed, non-peer reviewed, or the like. In some situations, computing device 104 may identify category using keyword matching.

Alternatively or additionally, and still referring to FIG. 1, for instance where keyword matching is inconclusive, and/or where keyword matching has been identified by reviewing users as inaccurate or unreliable, identifying category may include receiving category training data, the category training data including a plurality of entries, each entry including at least a portion of a work and a correlated category. "Training data," as used in this disclosure, is data containing correlations that a machine-learning and/or classification process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and further referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure. As a non-limiting illustrative example, theme training data 124 may include a plurality of entries including at least a portion of a work and a correlated category. "At least a portion" of a work may include any section, paragraph, keyword, or other textual element as described above.

Still referring to FIG. 1, training data may be retrieved, without limitation, from an expert database. Expert database may be implemented, without limitation, as a relational database, a key-value retrieval database such as a NOSQL database, or any other format or structure for use as a database that a person skilled in the art would recognize as suitable upon review of the entirety of this disclosure. Expert database may alternatively or additionally be implemented using a distributed data storage protocol and/or data structure, such as a distributed hash table or the like. Expert database may include a plurality of data entries and/or records as described above. Data entries in an expert database may be flagged with or linked to one or more additional elements of information, which may be reflected in data entry cells and/or in linked tables such as tables related by one or more indices in a relational expert database. Persons skilled in the art, upon reviewing the entirety of this disclosure, will be aware of various ways in which data entries in an expert database may store, retrieve, organize, and/or reflect data and/or records as used herein, as well as categories and/or populations of data consistently with this disclosure.

Figure 2:
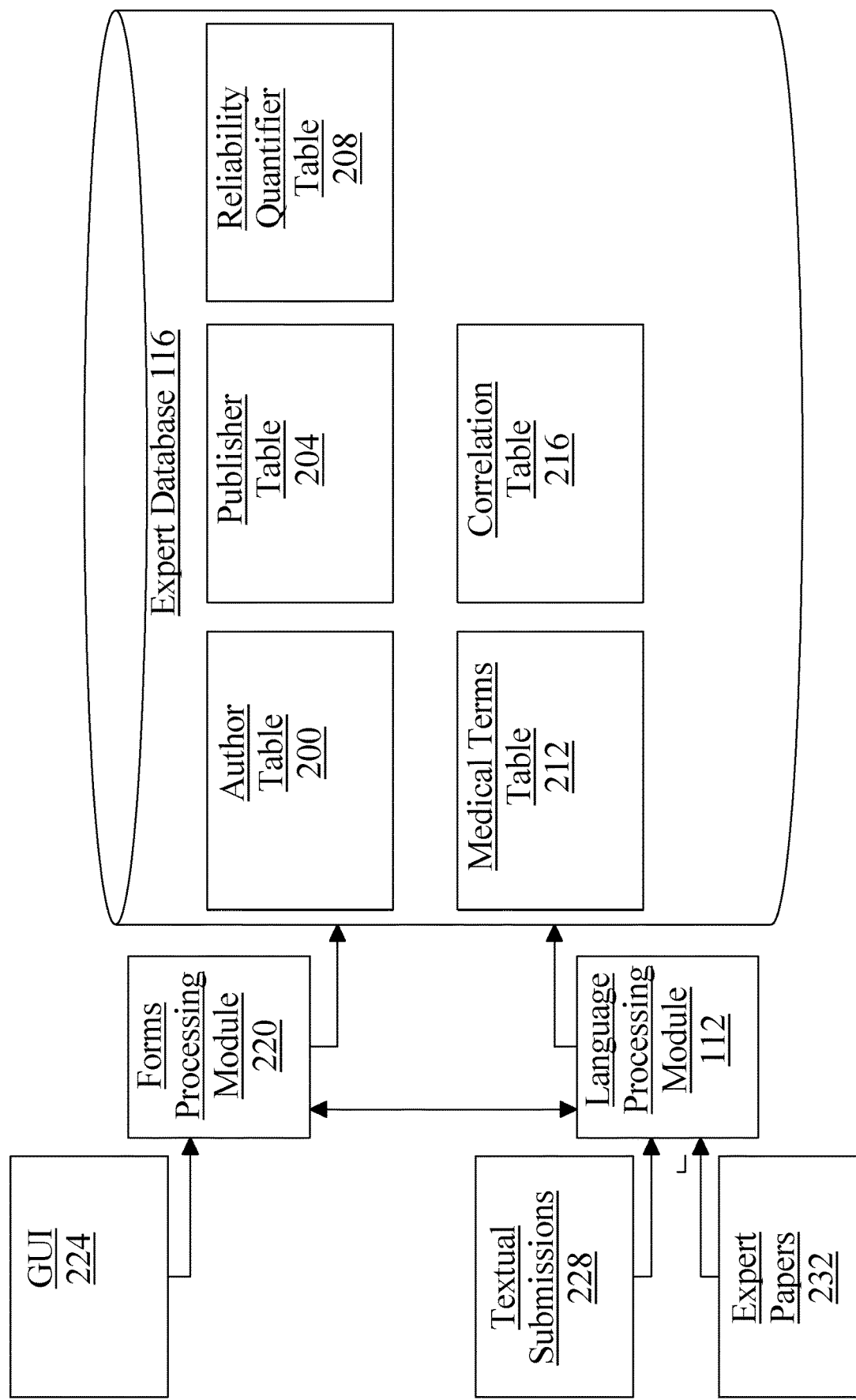
FIG. 2 is a block diagram illustrating an exemplary embodiment of an expert database.

Referring now to FIG. 2, an exemplary embodiment of an expert database is illustrated. Expert database may, as a non-limiting example, organize data stored in the expert database according to one or more database tables. One or more database tables may be linked to one another by, for instance, common column values. For instance, a common column between two tables of expert database may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in expert database may include, as a non-limiting example, an author information table 200, which may be used to store records indicating an identity of an author, a history of publications or other works by the author, one or more author themes, or the like. One or more tables may include a publisher table 204, which may store data describing identities of publishers, previously publisher themes, categories of publications ascribed to publishers, or the like. One or more tables may include a reliability quantifier table 208, in which scholastic works and related reliability quantifiers may be stored, including history of reliability quantifiers determined for accepted and/or rejected scholarly works as described below. One or more tables may include a medical terms table 121, which may contain a listing of terms and/or textual elements describing medical treatments, diagnostic elements, or the like. One or more tables may include a correlation table 216, which may be populated using correlations derived from scholarly works as described in further detail below; correlations may alternatively or additionally be populated in various tables as categorized by themes or other information according to which such correlations may be categorized.

In an embodiment, and still referring to FIG. 2, a forms processing module 220 may sort data entered in a submission via a graphical user interface 224 receiving expert submissions by, for instance, sorting data from entries in the graphical user interface 224 to related categories of data; for instance, data entered in an entry relating in the graphical user interface 224 to significance may be sorted into variables and/or data structures for impact score data, which may be provided to significance table 400, while data entered in an entry relating to temporal effects on events disease may be sorted into variables and/or data structures for the storage of such data, such as temporal effect, relative frequencies may be sorted to relative frequency table, and the like. Where data is chosen by an expert from pre-selected entries such as drop-down lists, data may be stored directly; where data is entered in textual form, a language processing module may be used to map data to an appropriate existing label, for instance using a vector similarity test or other synonym-sensitive language processing test to map data to existing labels and/or categories. Similarly, data from an expert textual submissions 228, such as accomplished by filling out a paper or PDF form and/or submitting narrative information, may likewise be processed using language processing module, and/or using processes and/or process steps as described in this disclosure.

Data may be extracted from expert papers 232, which may include without limitation publications in medical and/or scientific journals, by language processing module via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Referring again to FIG. 1, computing device 104 may be configured to identify a category of scholastic work by generating a category classifier 120, as a function of the training data, and identifying the scholastic work using the category classifier 120. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

Further referring to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may be configured to determine at least a work theme of scholastic work. As used in this disclosure, a "work theme" is a topic of scientific and/or medical research. Work theme may include a principal them, defined as a main topic of a work. Scholastic work may have a single work theme and/or a plurality of work themes; for instance, a single work may refer to a given treatment process or other protocol as alleviating a first condition, but also note and/or further describe another condition alleviated by the same treatment which is otherwise unrelated in literature and/or by specialty to the first condition. As a further example, scholastic work may be cross-disciplinary, and may thus contain content relating to two or more normally separate and/or siloed topic areas, which may be represented as two or more work themes.

With continued reference to FIG. 1, determining work theme may include receiving theme training data 124. Theme training data 124 may be implemented in any form suitable for implementation of category training data as described above. Theme training data 124 may include a plurality of entries. Each entry may include a training textual element and a correlated theme. A "training textual element," as used in this disclosure, is a textual element as defined above that is used as a training data entry. Computing device 104 may train a theme classifier 128 as a function of the training data. Theme classifier 128, which may be implemented as any classifier as described above, may take a plurality of textual elements as inputs, and output a work theme. Theme classifier 128 may be trained using any classification algorithm as described above. Computing device 104 may determine at least a work theme as a function of the plurality of textual elements and the theme classifier 128, for instance by inputting plurality of textual elements and outputting work theme. In an embodiment, computing device 104 may modify plurality of textual elements to match elements used in training data; for instance, computing device 104 may match words and/or phrases of plurality of textual elements to synonymous or otherwise semantically related words in training data. For instance, and without limitation, computing device 104 may match at least a textual element of plurality of textual elements to a training textual element as a function of a language processing module, for instance using vector similarity or the like. The matching training textual element may be used in place of the at least a textual element; in other words, computing device 104 may determine at least a work theme as a function of training textual element and theme classifier 128.

Still referring to FIG. 1, computing device 104 may be configured to calculate a reliability quantifier 132 of scholastic work. A "reliability quantifier 132," as used in this description, is a quantitative variable and/or field containing a number representing a degree to which a scholastic work may be relied upon as a good source of information, recommendations, training data, or the like. Computing device 104 may calculate reality quantifier using one or more data regarding scholastic work. For instance, computing device 104 may calculate reality quantifier may calculate as a function of the at least a work theme, the author, and the category. Computing device 104 may generate one or more numerical quantities which may be combined by addition and/or multiplication to derive reliability quantifier 132. As a non-limiting, illustrative example, reliability quantifier 132 may be initialized to a maximal value of 1 and each numerical quantity to be used to compute reliability score may be a number between 0 and 1 which may be multiplied by reliability quantifier 132 to furnish a final result between 0 and 1 which may be used to quantify reliability of scholastic work. As a further example, component quantities may be combined in a calculation performed using a machine-learning process and/or model; for instance, and without limitation, relationships between inputs as described below and reliability may be sufficiently complex as to render multiplication of factors insufficient to capture all cases, in which case a machine-learning process may be used to generate a more complex model that effectively captures such relationships to generate an accurate result.

Figure 3:
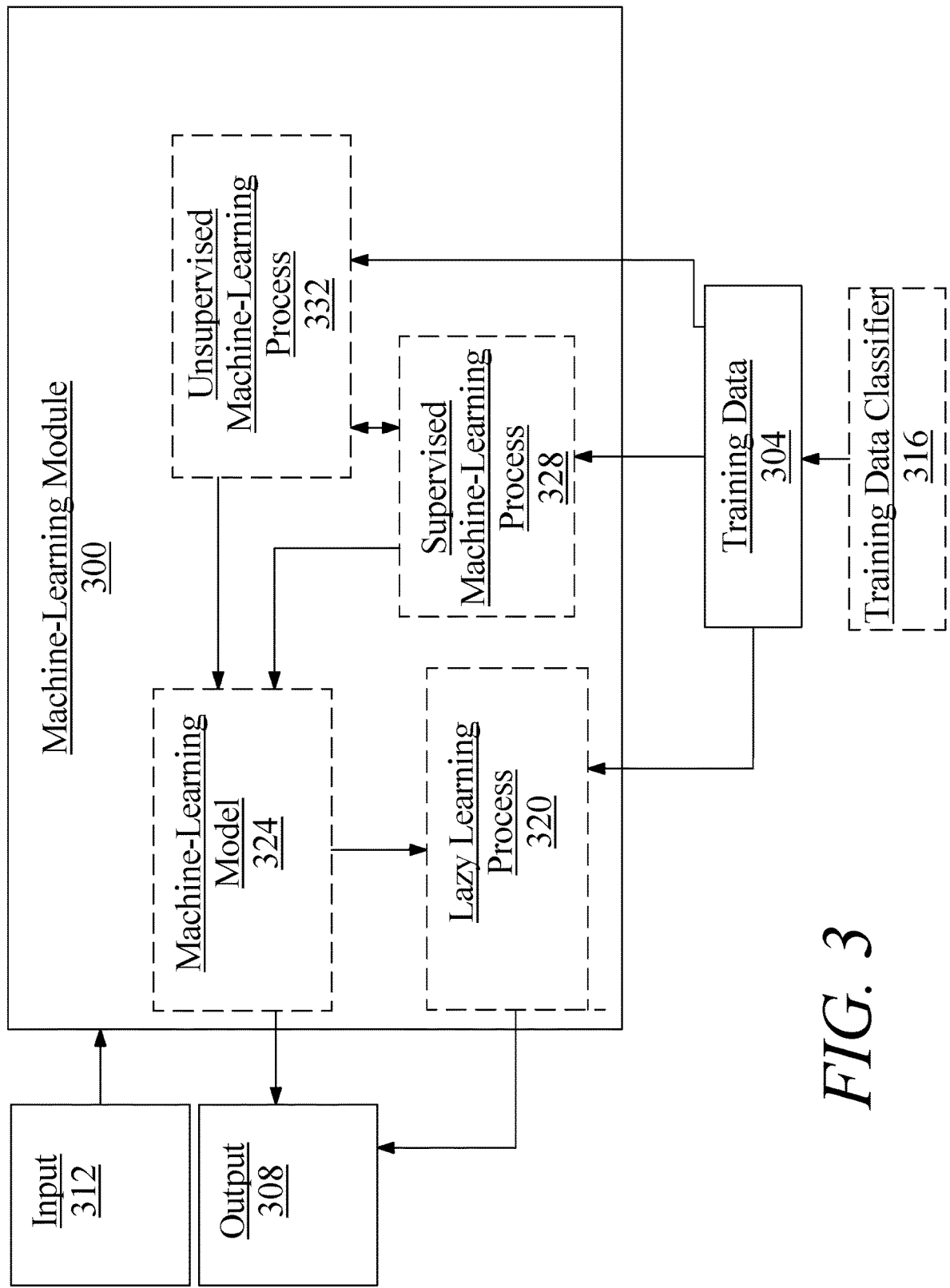
FIG. 3 is a block diagram illustrating an exemplary embodiment of a machine-learning module.

Referring now to FIG. 3, an exemplary embodiment of a machine-learning module 300 that may perform one or more machine-learning processes as described in this disclosure, is illustrated. Machine-learning module may include any suitable Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device 104/module to produce outputs 308 given data provided as inputs 312; this is in contrast to a non-machine learning software program where the commands to be executed are determined in advance by a user and written in a programming language.

In an embodiment, training data may be formed using one or more expert inputs; for instance, one or more experts may indicate that a given work, article, or the like of their choice represents an minimal state at which those experts would rely on the article, and associated reliability quantifier 132s may be aggregated, averaged, or the like to calculate a threshold number.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device 104 and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to one or more work themes.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning model 324s. A "machine-learning model 324," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs for calculation of reliability quantifier 132 as inputs, reliability quantifier 132 values as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 3, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 304.

Referring again to FIG. 1, one or more quantities used to determine reliability quantifier 132 may be calculated, without limitation, by determining a degree of similarly between at least a work theme and at least an author theme, where an "author theme" is a theme, such as any theme suitable for use as a work theme, typically addressed by author. Degree of similarity may be determined, without limitation, by using any distance metric suitable for use in a classifier as described above. Degree of similarity may be normalized to a value between 0 and 1. In an embodiment, at least an author theme may be stored in a database, such as without limitation expert database. Alternatively or additionally, one or more author themes may be determined using an author theme classifier 128. For instance, computing device 104 may receive a plurality of publications by the at least an author, to input to author theme classifier 128. Computing device 104 may training author theme classifier 128, using the theme training data 124; author theme classifier 128 may accept publications and/or textual elements as inputs and output author themes. Computing device 104 may identify at least an author theme as a function of the plurality of publications and the author theme classifier 128, by inputting plurality of author publications to author theme classifier 128.

Alternatively or additionally, and still referring to FIG. 1, one or more quantities used to determine reliability quantifier 132 may be calculated, without limitation, by determining a degree of similarly between at least a work theme and at least an publication theme, where an "publication theme" is a theme, such as any theme suitable for use as a work theme, typically addressed in a publication in which scholastic work appears. Degree of similarity may be determined, without limitation, by using any distance metric suitable for use in a classifier as described above. Degree of similarity may be normalized to a value between 0 and 1. In an embodiment, at least a publication theme may be stored in a database, such as without limitation expert database. At least a publication theme may be determined, as a non-limiting example, by identifying one or more phrases in a header of publication and/or in a field of data provided with and/or concerning publication, indicating a theme and/or principal theme to which the publication is dedicated, such as a field of science, medicine, or the like. Alternatively or additionally, determining at least a publisher theme may include receiving a plurality of publications of the publisher. Computing device 104 may train a publisher theme classifier 128 using theme training data 124; publisher theme classifier 128 may receive plurality of publications as inputs an output at least a publisher theme. Computing device 104 may identify at least a publisher theme as a function of the plurality of publications and the publisher theme classifier 128.

With continued reference to FIG. 1, computing device 104 may generate one or more additional quantities for computation of reliability quantifier 132. One or more quantities may include, without limitation, a quantity representing document type, which may be normalized as above. For instance, and without limitation, a greater quantity may be associated with a peer reviewed journal article, a lesser quantity with a non-peer reviewed journal article, a lesser quantity still with a non-journal article, and a still lesser quantity with a webpage; thus, as a non-limiting example and all other factors being equal, if scholastic work is a peer reviewed journal article, it may have a higher reliability quantifier 132 than if it is a popular science article.

Still referring to FIG. 1, one or more quantities may include, without limitation, a quantity representing publication type, which may be normalized as above. For instance, and without limitation, a greater quantity may be associated with a specialized publication, defined as a publication having a narrow focus on a range of similar publication themes, where "similarity" may be determined using distance metrics as described above. Continuing the example, a lesser quantity may be associated with a non-specialized journal, such as a journal having publisher themes that are more divergent according to distance metrics as described above. Further continuing the example, a non-scientific periodical such as a popular science and/or news publication may receive a still lesser quantity.

Continuing to refer to FIG. 1, one or more quantities may include, without limitation, one or more prestige factors, where a "prestige factor" is defined as a factor based on rating in a scientific and/or medical community of an author and/or publication. For instance, a journal prestige factor may be higher and/or greater for a journal recognized as prestigious, reliable, and/or influential than for a journal that is less recognized; journal prestige factor may be measurable at various gradations representing various degrees of journal prestige. As another example, an expert prestige factor may be higher and/or greater for an author recognized as prestigious, reliable, and/or influential than for an author that is less recognized; expert prestige factor may be measurable at various gradations representing various degrees of author prestige. Author prestige may be calculated without limitation by receiving a plurality of ratings by other experts of author and averaging or otherwise aggregating such ratings.

With further reference to FIG. 1, at least a work theme may include a first work theme and a second work theme, and/or any number of additional work themes; computing device 104 may calculate a first reliability quantifier 132 for the first work theme and a second reliability quantifier 132 for the second work theme. For instance, scholastic work may be given a higher reliability quantifier 132 with regard to first work theme because first work theme may have a greater similarity to author theme and/or publisher theme; scholastic work may be given a lower reliability quantifier 132 with regard to second work theme because of a lesser degree of similarity between second work theme and author theme and/or publisher theme. Persons skilled in the art, upon reviewing the entirety of this disclosure, will be aware of various ways in which a first work theme may result in a different reliability quantifier 132 from a second work theme, based on quantities that may be calculated per theme as described above. Alternatively, there may be a reliability quantifier 132 per theme, which may be aggregated, for instance and without limitation by averaging or the like, to produce an overall reliability quantifier 132.

Still referring to FIG. 1, computing device 104 is configured to select the scholastic work as a function of the reliability quantifier 132. For instance, and without limitation, computing device 104 may compare reliability quantifier 132 to a preconfigured threshold number. Threshold number may be set based on one or more expert inputs; for instance, one or more experts may indicate that a given work, article, or the like of their choice represents an minimal state at which those experts would rely on the article, and associated reliability quantifier 132s may be aggregated, averaged, or the like to calculate a threshold number. Alternatively or additionally, threshold number may be an average or other aggregated value of reliability quantifier 132s of works already selected.

With continued reference to FIG. 1, threshold may be calculated for comparison to single reliability quantifier 132 calculated per document. Alternatively or additionally, a different threshold may be calculated for each work theme as described above. A reliability quantifier 132 of each theme may be compared to a threshold corresponding to that theme. As a result, scholastic work may be accepted for one work theme and rejected for another work theme.

Still referring to FIG. 1, where scholastic work is rejected for failing to meet a threshold, no further process steps may be performed with regard to that work; alternatively or additionally, an entry indicating reliability quantifier 132 and/or rejected status of work may be stored in expert database. Where at least a reliability quantifier 132 is accepted, computing device 104 is configured to derive, from scholastic work, at least a correlation between a diagnostic element, defined for purposes of this disclosure as any diagnosis, prognosis, prognostic element, test result, or other data suitable for identifying a disease state currently suffered and/or likely to occur in the future and a practice, where a "practice" as used herein is any action or combination of actions to alleviate and/or prevent a disease state indicated by prognostic element. Derivation may be performed by analysis of language of scholarly work to identify one or more recommendations; for instance one or more recommendations may include text associated with an introductory statement, paragraph introduction, and/or point heading that has a high statistical correlation with recommendations, such as without limitation a term like "recommendation," "we recommend," or the like. Such correlations may be identified by language processing module, and blocks of text containing recommendations may be identified by entry of one or more such terms by an expert or other user; other correlated terms may be identified using correlations, permitting language module to find such recommendations. In an embodiment, and still referring to FIG. 1, computing device 104 may extract and/or identify correlations in specific sections, a conclusion, an abstract, or the like, and may subsequently locate and/or identify corresponding or related text in analysis to further aid in accuracy of identified correlations.

Alternatively or additionally, correlation may be identified in scholastic work by matching at least a statement and/or paragraph in scholastic work to an action that may be recommended, such as without limitation a medical treatment or the like. For instance, expert database may include a listing of terms and/or textual elements describing medical treatments or the like; such terms and/or textual elements may matched to one or more textual elements within scholastic work using language processing module using any suitable relationship as described above, including without limitation vector similarity. Sentences and/or paragraphs containing terms so identified may be treated as blocks of text containing correlations. As a further example, terms associated with positive and/or negative results may be stored in expert database or other suitable datastore, related and/or synonymous terms may be identified using language processor, and blocks of text containing terms so identified may be identified as containing potential correlations.

Further referring to FIG. 1, blocks of text containing recommendations and/or other material used for correlations may additionally be parsed for terms and/or other textual elements associated with a theme, as identified using work theme classifier 128 and/or using language processing module; blocks of text containing recommendation may be used to derive at least a correlation only where such blocks are matched and/or classified using work theme classifier 128 to a work theme for which scholastic work has an associated reliability quantifier 132 exceeding a work theme-specific threshold.

Still referring to FIG. 1, derivation of correlation may further include extraction of a first element indicating a condition, symptom, and/or biological extraction and a second element indicating an action that is recommended and/or an action that is not recommended with regard to a person presenting with the identified condition, symptom, and/or biological extraction. Biological extraction and/or receipt thereof may be implemented in any manner disclosed in U.S. Nonprovisional application Ser. No. 16/865,740, filed on May 4, 2020, and entitled "METHODS AND SYSTEMS FOR SYSTEM FOR NUTRITIONAL RECOMMENDATION USING ARTIFICIAL INTELLIGENCE ANALYSIS FOR IMMUNE IMPACTS," the entirety of which is incorporated herein by reference. Action may include, without limitation administration of a given treatment, course of treatments, pharmaceutical dosage and/or prescription, a recommended therapy, a recommended nutritional input, a surgical procedure, a course of physical therapy, an exercise program or other recommended fitness-related action, a recommended lifestyle change such as cessation of substance abuse, increased sleep, or the like, and/or any other action for the alleviation and/or improvement of one or more conditions, symptoms or health risks that may occur to persons skilled in the art upon reviewing the entirety of this disclosure.

Further referring to FIG. 1, an element of text indicating an action and/or a diagnostic element may be associated with textual element describing the same action that has been stored in previously recorded entries in an expert database. Association may be performed, without limitation, using language processing module, which may identify synonymous terms, phrases, and/or blocks of text according to any process as described above. A new entry in expert database may be generated using identified diagnostic element and a correlated action determined as above; in an embodiment either or both of diagnostic element and correlated action may be replaced by identified associated terms, which may, for instance, enable training data generated therefrom to use a smaller set of selected terms, which may in turn improve accuracy and/or efficiency of subsequent machine-learning and/or classification processes that may be performed using resulting training data.

In an embodiment, and still referring to FIG. 1, language processing module may be used to distinguish between positive recommendations and negative recommendations. In an embodiment, this may be performed by detection of words and/or phrases that function as negations, such as "not," "no effect," "negligible effect," or the like. Alternatively or additionally, phrase comparison and/or placement within language processing module objects such as vector space may include phrases that contain negations and/or other terminology that acts to indicate that an action is disfavored. As a further example, statistical correlations and/or mathematical associations may include probabilistic formulas or relationships indicating a positive and/or negative association between at least an extracted word and/or a given action; positive or negative indication may include an indication that a given document is or is not recommending an action. For instance, and without limitation, a negative indication may be determined from a phrase such as "increased physical activity was not found to be an effective way to slow progression of dementia," whereas a positive indication may be determined from a phrase such as "increased physical activity was found to be an effective way to slow progression of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory of computing device 104, or the like.

In an embodiment, and with continued reference to FIG. 1, one or more selected correlations may be inspected by a user, such as an expert user; expert user may verify that an inspected correlation accurately reflects a recommendation and/or finding in scholastic work. Where expert indicates correlation is inaccurate, expert may enter an indication indicating inaccuracy and/or an alternative correlation that is more accurate; such entries by expert may be used to train language processing module further, modifying one or more associations used to identify and/or characterize correlations. Entries may alternatively or additionally be used to generate alternative correlations, for instance as entered by reviewing user.

Still referring to FIG. 1, computing device 104 is configured to store the at least a correlation in an expert database. A record may be stored, for instance in expert database indicating correlation. Additional elements of data may be stored with correlation, including without limitation a reliability quantifier 132 associated with scholastic work generally and/or with regard to a related work them. Additional elements may include one or more work themes identified as associated with correlation. Additional elements may include an identifier of scholastic work, which may for instance be used in further processing regarding entry and/or scholastic work as described in further detail below. For instance, and without limitation, computing device 104 may perform modification and/or removal of entries from expert database as described below, based, without limitation, upon retractions and/or negative citations.

Further referring to FIG. 1, computing device 104 may be configured to use correlation and/or scholastic work to create one or more training data elements. For instance, an association with scholastic work with a work theme may be recorded as theme training data 124, entries of which may associate textual elements of scholastic work with one or more work themes; this may be used to further train theme classifier 128 using methods as described above. Correlation may be used in training data for further classification and/or machine-learning processes used for instance to recommend treatments or other ameliorative processes for alleviation, cure, and/or treatment of conditions associated with diagnostic elements as described above. Training data entries so used may, in a non-limiting example, be weighted by reliability quantifier 132; this may, for instance, enable resulting machine-learning processes and/or classifiers to generate models using algorithms that account for such weighting, which may result in greater accuracy.

Figure 4:
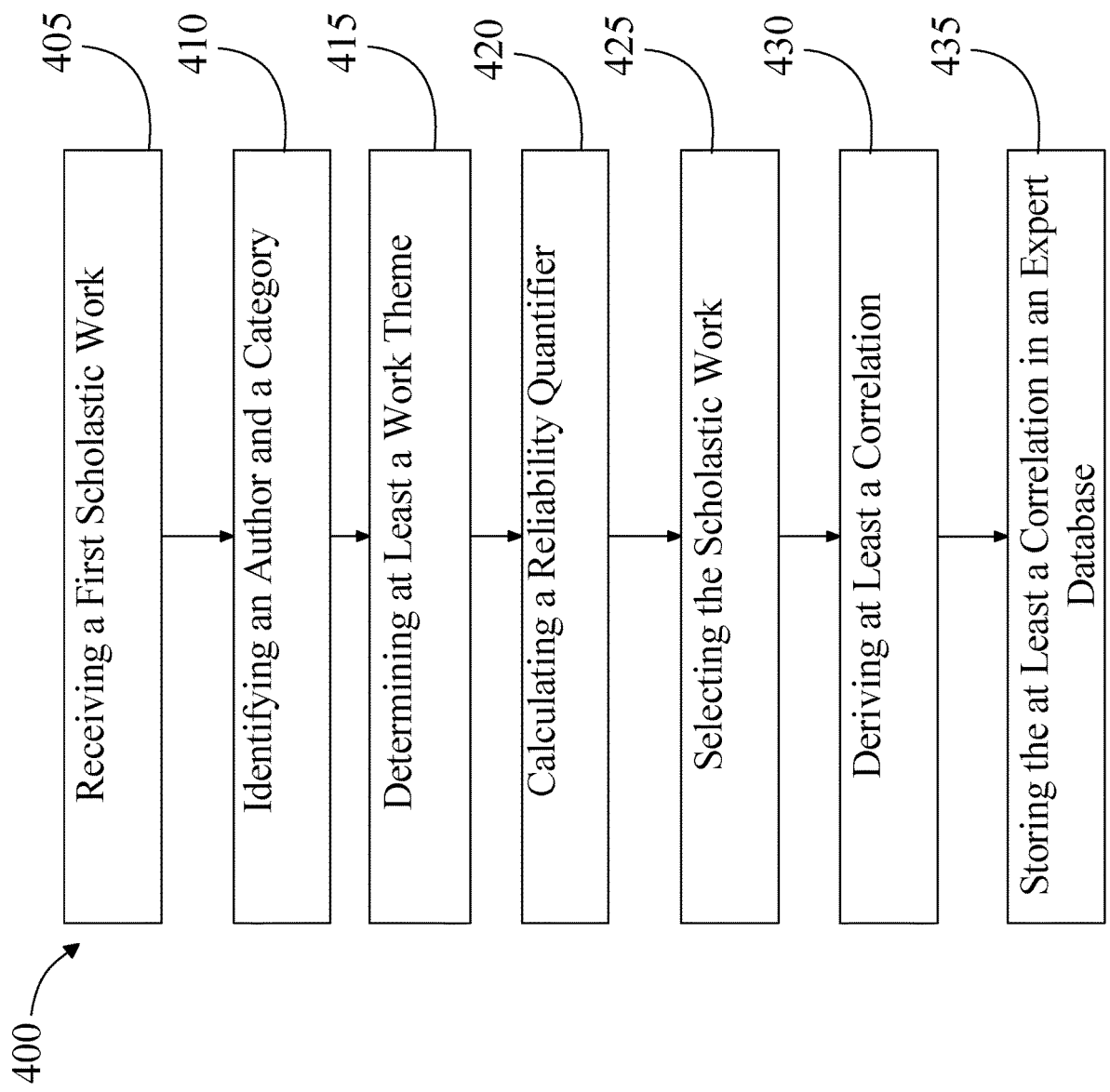
FIG. 4 is a flow diagram illustrating an exemplary embodiment of a method of classification of scholastic works.

Referring now to FIG. 4, an exemplary embodiment of a method 400 of classification of scholastic works is illustrated. At step 405, a computing device 104 receives a first scholastic work 108 including a plurality of textual elements; this may be implemented, without limitation, as described above in reference to FIGS. 1-4.

At step 410, and still referring to FIG. 4, computing device 104 identifies an author and a category; this may be implemented, without limitation, as described above in reference to FIGS. 1-4. Identifying category may include receiving category training data, which may include a plurality of entries. Each entry may include at least a portion of a work and a correlated category. Computing device 104 may generate a category classifier 120, as a function of the training data. Computing device 104 may identify the scholastic work using the category classifier 120.

With continued reference to FIG. 4, at step 415 computing device 104 determines at least a theme; this may be implemented, without limitation, as described above in reference to FIGS. 1-4. Determining may include receiving theme training data 124. Theme training data 124 including a plurality of entries, each entry including a training textual element and a correlated theme. Determining may include training a theme classifier 128 as a function of the training data. Determining may include determining the at least a work theme as a function of the plurality of textual elements and the theme classifier 128. Determining the at least a theme may include matching at least a textual element of the plurality of textual elements to a training textual element as a function of a language processing module and determining the at least a work theme as a function of the training textual element and the theme classifier 128.

At step 420, and still referring to FIG. 4, computing device 104 calculates a reliability quantifier 132 as a function of the at least a theme, the author, and the category; this may be implemented, without limitation, as described above in reference to FIGS. 1-4. Calculating the reliability quantifier 132 may include receiving a plurality of publications by the at least an author, training an author theme classifier 128 using the theme training data 124, and identifying at least an author theme as a function of the plurality of publications and the author theme classifier 128. Computing device 104 may compare at least an author theme to work theme. Computing device 104 may calculate reliability quantifier 132 as a function of the comparing. Calculating reliability quantifier 132 may include identifying a publisher of the first scholastic work 108. Computing device 104 may determine at least a publisher theme of publisher. Determining at least a publisher theme may include receiving a plurality of publications of the publisher, training a publisher theme classifier 128 using the theme training data 124, and identifying the at least a publisher theme as a function of the plurality of publications and the publisher theme classifier 128. Computing device 104 may compare at least a publisher theme to the theme. Computing device 104 may calculate reliability quantifier 132 as a function of the comparing. In an embodiment, at least a theme may include a first theme and a second theme, and computing device 104 may calculate a first reliability quantifier 132 for the first theme and a second reliability quantifier 132 for the second theme.

At step 425, computing device 104 selects scholastic work as a function of reliability quantifier 132; this may be implemented, without limitation, as described above in reference to FIGS. 1-4. At step 430, computing device 104 derives at least a correlation between a diagnostic element and a practice from the scholastic work; this may be implemented, without limitation, as described above in reference to FIGS. 1-4.

At step 435, computing device 104 stores at least a correlation in an expert database; this may be implemented, without limitation, as described above in reference to FIGS. 1-4.

Figure 5:
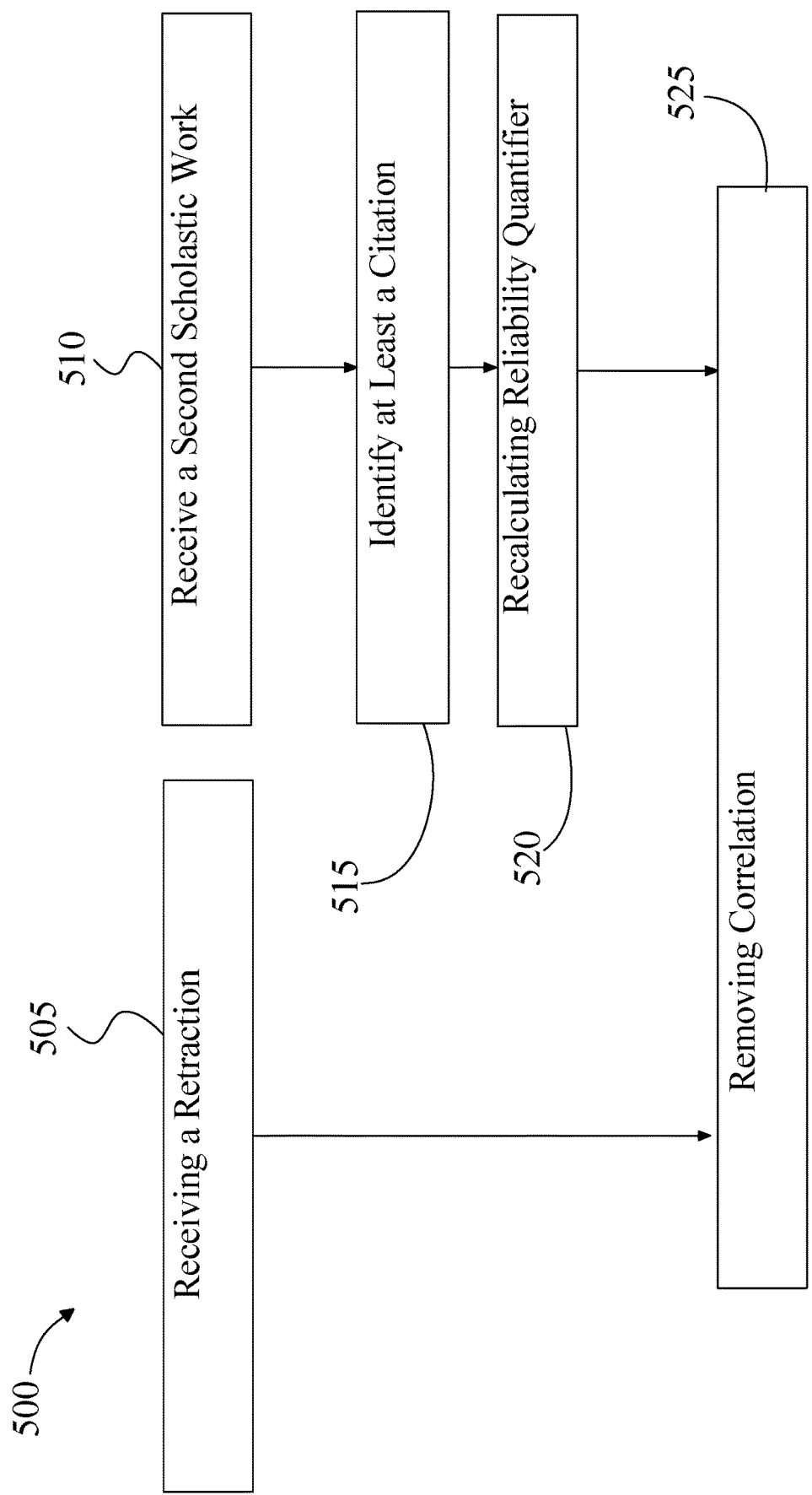
FIG. 5 is a flow diagram illustrating an exemplary embodiment of a method of modifying an expert database.

Referring now to FIG. 5, an exemplary embodiment of a method 500 of modifying an expert database is illustrated. At step 505, Computing device 104 may receive a retraction of first scholastic work 108 and remove at least a correlation from the expert database. At step 510 computing device 104 may receive a second scholastic work. At step 515, computing device 104 may identify at least a citation of first scholastic work 108 in the second scholastic work. At step 520, computing device 104 may recalculate reliability quantifier 132 and/or quantifiers as a function of the at least a citation. At step 525, computing device 104 may remove at least a correlation from expert database as a function of the reliability quantifier 132, for instance as recalculated. For instance, correlations may be tagged with identifier of a scholastic work from which they were derived, and thus may be removed where scholastic work has been disqualified.

It is to be noted that any one or more of the aspects and embodiments described herein may be conveniently implemented using one or more machines (e.g., one or more computing devices that are utilized as a user computing device 104 for an electronic work, one or more server devices, such as a work server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device 104) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device 104) and any related information (e.g., data structures and data) that causes the machine to perform any one of the methodologies and/or embodiments described herein.

Examples of a computing device 104 include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device 104 may include and/or be included in a kiosk.

Figure 6:
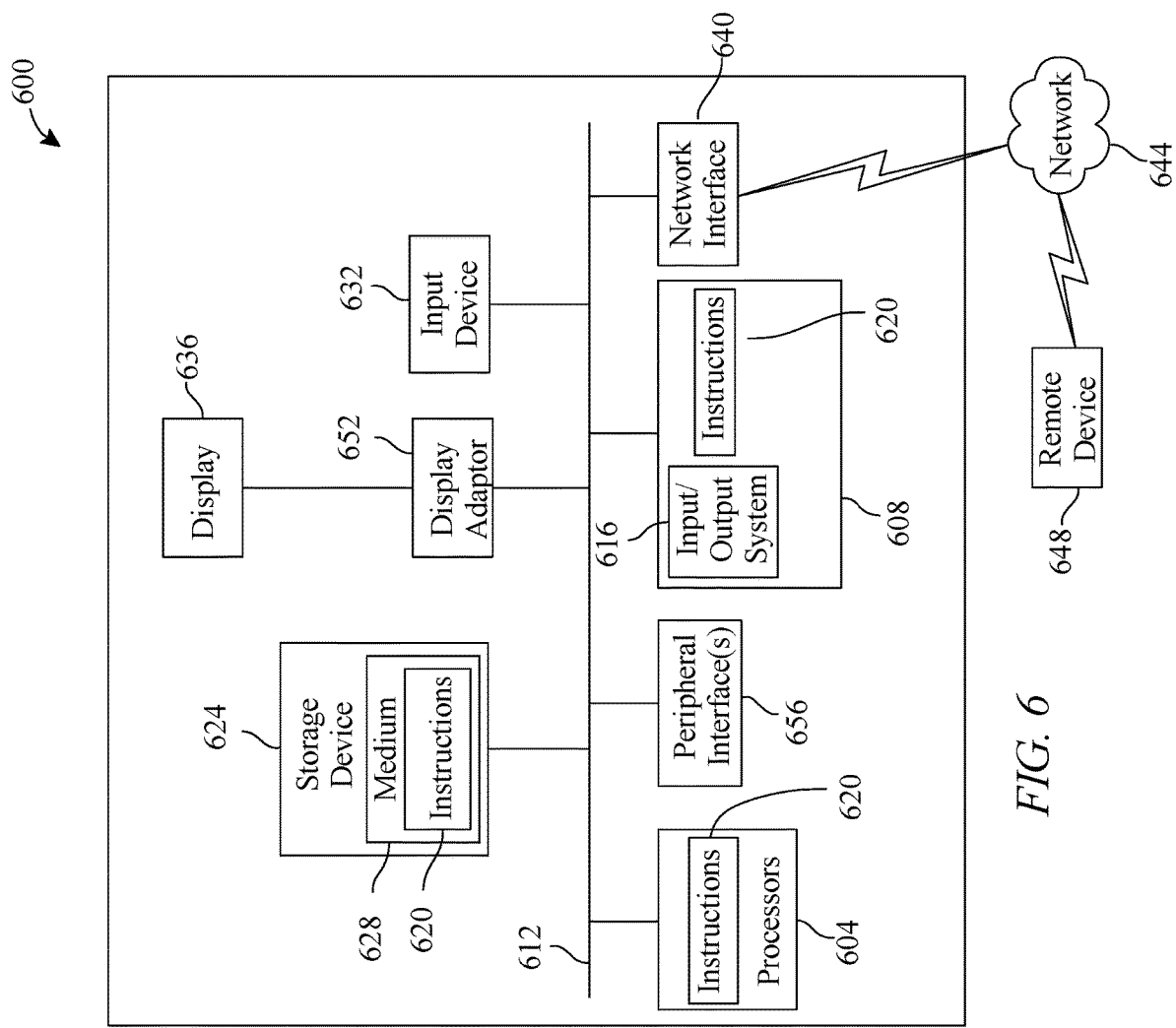
FIG. 6 is a block diagram of a computing system that can be used to implement any one or more of the methodologies disclosed herein and any one or more portions thereof.

FIG. 6 shows a diagrammatic representation of one embodiment of a computing device 104 in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIRE-WIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for classification of scholastic works, the system comprising a computing device, wherein the computing device is configured to:
   receive a first scholastic work including a plurality of textual elements;
   identify an author and a category of the first scholastic work;
   determine at least a work theme, wherein determining further comprises:
      receiving theme training data, the theme training data including a plurality of entries, each entry including a training textual element and a correlated theme;
      training a theme classifier as a function of the training data; and
      determining the at least a work theme as a function of the plurality of textual elements and the theme classifier;
   calculate a reliability quantifier as a function of the at least a theme, the author, and the category;
   select the scholastic work as a function of the reliability quantifier;
   derive, from the scholastic work, at least a correlation between a diagnostic element and a practice; and
   store the at least a correlation in an expert database.

2. The system of claim 1, wherein identifying the category further comprises:
   receiving category training data, the category training data including a plurality of entries, each entry including at least a portion of a work and a correlated category;
   generating, by the computing device, a category classifier, as a function of the training data; and
   identifying the scholastic work using the category classifier.

3. The system of claim 1 wherein determining the at least a theme further comprises:
   matching at least a textual element of the plurality of textual elements to a training textual element as a function of a language processing module; and
   determining the at least a work theme as a function of the training textual element and the theme classifier.

4. The system of claim 1, wherein calculating the reliability quantifier further comprises:
   receiving a plurality of publications by the at least an author;
   training an author theme classifier using the theme training data;
   identifying at least an author theme as a function of the plurality of publications and the author theme classifier;
   comparing the at least an author theme to the theme; and
   calculating the reliability quantifier as a function of the comparing.

5. The system of claim 1, wherein calculating the reliability quantifier further comprises:
   identifying a publisher of the first scholastic work;
   determining at least a publisher theme of the publisher;
   comparing the at least a publisher theme to the theme; and calculating the reliability quantifier as a function of the comparing.

6. The system of claim 5, wherein determining the at least a publisher theme further comprises:
receiving a plurality of publications of the publisher;
training a publisher theme classifier using the theme training data; and
identifying the at least a publisher theme as a function of the plurality of publications and the publisher theme classifier.

7. The system of claim 1, wherein the at least a theme includes a first theme and a second theme, and further comprising calculating a first reliability quantifier for the first theme and a second reliability quantifier for the second theme.

8. The system of claim 1, wherein the computing device is further configured to:
receive a retraction of the first scholastic work; and
remove the at least a correlation from the expert database.

9. The system of claim 1, wherein the computing device is further configured to:
receive a second scholastic work;
identify at least a citation of the first scholastic work in the second scholastic work; and
recalculate the reliability quantifier as a function of the at least a citation.

10. The system of claim 9, wherein the computing device is further configured to remove the at least a correlation from the expert database as a function of the reliability quantifier.

11. A method of classification of scholastic works, the method comprising:
receiving, at a computing device, a first scholastic work including a plurality of textual elements;
identifying, by the computing device, an author and a category of the first scholastic work;
determining, by the computing device, at least a work theme, wherein determining further comprises:
receiving theme training data, the theme training data including a plurality of entries, each entry including a training textual element and a correlated theme;
training a theme classifier as a function of the training data; and
determining the at least a work theme as a function of the plurality of textual elements and the theme classifier;
calculating, by the computing device, a reliability quantifier as a function of the at least a theme, the author, and the category;
selecting, by the computing device, the scholastic work as a function of the reliability quantifier;
deriving, by the computing device and from the scholastic work, at least a correlation between a diagnostic element and a practice; and
storing, by the computing device the at least a correlation in an expert database.

12. The method of claim 11, wherein identifying the category further comprises:
receiving category training data, the category training data including a plurality of entries, each entry including at least a portion of a work and a correlated category;
generating, by the computing device, a category classifier, as a function of the training data; and
identifying the scholastic work using the category classifier.

13. The method of claim 11 wherein determining the at least a theme further comprises:
matching at least a textual element of the plurality of textual elements to a training textual element as a function of a language processing module; and
determining the at least a work theme as a function of the training textual element and the theme classifier.

14. The method of claim 11, wherein calculating the reliability quantifier further comprises:
receiving a plurality of publications by the at least an author;
training an author theme classifier using the theme training data;
identifying at least an author theme as a function of the plurality of publications and the author theme classifier;
comparing the at least an author theme to the theme; and
calculating the reliability quantifier as a function of the comparing.

15. The method of claim 11, wherein calculating the reliability quantifier further comprises:
identifying a publisher of the first scholastic work;
determining at least a publisher theme of the publisher;
comparing the at least a publisher theme to the theme; and
calculating the reliability quantifier as a function of the comparing.

16. The method of claim 15, wherein determining the at least a publisher theme further comprises:
receiving a plurality of publications of the publisher;
training a publisher theme classifier using the theme training data; and
identifying the at least a publisher theme as a function of the plurality of publications and the publisher theme classifier.

17. The method of claim 11, wherein the at least a theme includes a first theme and a second theme, and further comprising calculating a first reliability quantifier for the first theme and a second reliability quantifier for the second theme.

18. The method of claim 11 further comprising:
receiving a retraction of the first scholastic work; and
removing the at least a correlation from the expert database.

19. The method of claim 11 further comprising:
receiving a second scholastic work;
identifying at least a citation of the first scholastic work in the second scholastic work; and
recalculating the reliability quantifier as a function of the at least a citation.

20. The method of claim 19 further comprising removing the at least a correlation from the expert database as a function of the reliability quantifier.

* * * * *